United States Patent [19]

Endo et al.

[11] Patent Number: 5,223,416
[45] Date of Patent: Jun. 29, 1993

[54] PROCESS FOR PRODUCING R(−)-MANDELIC ACID AND DERIVATIVES THEREOF

[75] Inventors: Takakazu Endo; Koji Tamura, both of Kanagawa, Japan

[73] Assignee: Nitto Chemical Industry Co., Ltd., Tokyo, Japan

[21] Appl. No.: 677,175

[22] Filed: Mar. 29, 1991

[30] Foreign Application Priority Data

Mar. 30, 1990 [JP] Japan .................................. 2-80694
Aug. 16, 1990 [JP] Japan .................................. 2-214914
Aug. 16, 1990 [JP] Japan .................................. 2-214915

[51] Int. Cl.$^5$ ........................ C12P 7/42; C12P 13/00; C12P 41/00; C12P 11/00
[52] U.S. Cl. .................... 435/128; 435/130; 435/146; 435/280; 435/822; 435/829; 435/839; 435/840; 435/872; 435/874
[58] Field of Search ............... 435/280, 128, 130, 146, 435/822, 874, 829, 840, 872, 839

[56] References Cited

FOREIGN PATENT DOCUMENTS 0356912 5/1989 European Pat. Off. .
0348901 1/1990 European Pat. Off. .

OTHER PUBLICATIONS

Derwent Abs. 88-303602/43 Idemitsu Kosan KK J63222696 (Sep. 1988).
Hiromichi Ohta et al., "Microbial Hydrolysis of Substituted . . . Ethanolamines", Agricultural and Biological Chemistry, vol. 53, No. 1, Jan. 1989, Tokyo, Japan, pp. 281-283.
World Patents Index Latest, Week 9203, Derwent Publications Ltd., London, GB; AN 92-029694 & JP-A-3 277 292 (Aishi Chemical) Dec. 9, 1991.

*Primary Examiner*—Herbert J. Lilling
*Attorney, Agent, or Firm*—Sughrue, Mion, Zinn, Macpeak & Seas

[57] ABSTRACT

A process for the predominantly producing R(−)-mandelic acid or a derivative thereof which comprises subjecting (i) R,S-mandelonitrile or a derivative thereof, or (ii) a mixture of prussic acid and benzaldehyde or a derivative of benzaldehyde to the action of a microorganism selected from the group consisting of the genus Aureobacterium, Pseudomonas, Caseobacter, Alcaligenes, Acinetobacter, Brevibacterium, Nocardia, and Bacillus or treated cells thereof, which the microorganism is capable of stereospecifically hydrolyzing a nitrile group of the R,S-mandelonitrile or a derivative thereof, in a neutral or basic aqueous reaction system to produce the R(−)-mandelic acid.

10 Claims, No Drawings

PROCESS FOR PRODUCING R(−)-MANDELIC ACID AND DERIVATIVES THEREOF

FIELD OF THE INVENTION

This invention relates to a process for producing R(−)-mandelic acid or a derivative thereof. More particularly, it relates to a process for preparing R(−)-mandelic acid or a derivative thereof represented by formula (I) shown below by the action of a microorganism capable of asymmetrically hydrolyzing a nitrile group of R,S-mandelonitrile or a derivative thereof represented by formula (II) shown below. R(−)-Mandelic acid and its derivatives of the present invention are of industrial importance as starting materials for synthesizing a variety of pharmaceuticals and agricultural chemicals.

BACKGROUND OF THE INVENTION

Known processes for producing R(−)-mandelic acid from chemically synthesized R,S-mandelic acid (i.e., a racemate) include (1) racemic resolution by fractional crystallization (see JP-A-58-177933, the term "JP-A" as used herein means an "unexamined published Japanese patent application"), (2) racemic resolution by chromatography (see, European Patent Publication No. 98 707A), (3) racemic resolution of a racemate ester by enzymatic asymmetric hydrolysis (see, K. Mori, et al., *Tetrahedron*, Vol. 36, p. 91 (1980)), and (4) chemical asymmetric synthesis by using a chiral reagent (see, D.A. Evans, et al., *J. Am. Chem. Soc.*, Vol. 107, p. 4346 (1985)).

Known biological processes for producing R(−)-mandelic acid include, in addition to the above-described asymmetric hydrolysis of a racemic ester, (5) microbial asymmetric reduction of benzoylformic acid (see JP-A-57-198096). Further, known biological processes for producing R(−)-mandelic acid and its derivatives include (6) hydrolysis of R(−)-mandelonitrile or a substituted R(−)-mandelonitrile which is obtained by asymmetric synthesis using D-oxynitrilase (see JP-A-63-219388 and JP-A-2-5885) and (7) asymmetric hydrolysis of mandelonitrile or a substituted mandelonitrile or mandelamide or a substituted mandelamide by the action of a microorganism belonging to the genus Alcaligenes, Pseudomonas, Rhodopsuedomonas, Corynebacterium, Acinetobacter, Bacillus, Mycobacterium, Rhodococcus, or Candida (see, JP-A-84198 corresponding to European Patent Publication No. 0 348 901 A).

All of processes (1) to (3), consisting of racemic resolution, involve complicated steps which cause a reduction in yield for every step. Process (4), consisting of asymmetric synthesis, requires use of an expensive chiral reagent as a catalyst and does not yield products of high optical purity. Biological process (5), consisting of asymmetric reduction of benzoylformic acid, inherently contains difficulties in synthesizing a substrate and maintaining an NADH reconstitution system. The disclosure for process (6), called a D-oxynitrilase process, is no more than a statement that optically active mandelic acid or substituted mandelic acid has been obtained, additional follow-up studies are needed before industrialization would be possible. Process (7), consisting of asymmetric hydrolysis of mandelonitrile, a substituted mandelonitrile, mandelamide, or a substituted mandelamide does not produce one optically active compound directly from a racemate predominantly over the other optically active compound and hence involves handling both optically active compounds together. According to the disclosure of JP-A-2-84198 supra, the unreacted residual nitrile or amide having the undesired optical activity is recovered and converted to an organic acid having the opposite optical activity by acid hydrolysis or to a racemate by alkali treatment; this product is then used as a starting material for the production of R(−)-mandelic acid.

Such procedures for the separation of residual mandelonitrile or mandelamide, etc. of the other opposite activity and for racemization by alkali treatment make for a complicated process, which ultimately reduces the yield. Moreover, JP-A-2-84198 gives no specific example for production of an R(−)-mandelic acid derivative from a substituted mandelonitrile, leaving open the question as to whether an R(−)-mandelic acid derivative could be obtained with efficiency and high optical purity.

Thus, known processes are unsatisfactory for the industrial production of R(−)-mandelic acid and derivatives thereof.

SUMMARY OF THE INVENTION

The inventors have conducted extensive investigations in order to develop an industrial process for producing R(−)-mandelic acid and its derivatives by starting with (i) R,S-mandelonitrile or a derivative thereof or (ii) a mixture of prussic acid and benzaldehyde or a derivative of benzaldehyde. As a result, they have found that R(−)-mandelic acid or a derivative thereof can be obtained almost stoichiometrically by reacting, in a neutral or basic aqueous solution, (i) R,S-mandelonitrile or a derivative thereof or (ii) a mixture of prussic acid and benzaldehyde or a derivative of benzaldehyde with a microorganism capable of stereospecifically hydrolyzing a nitrile which belongs to the genus Aureobacterium, Pseudomonas, Caseobacter, Alcaligenes, Acinetobacter, Brevibacterium, Nocardia, or Bacillus.

More specifically, the present invention involves a process for predominantly producing R(−)-mandelic acid or a derivative thereof represented by formula (I):

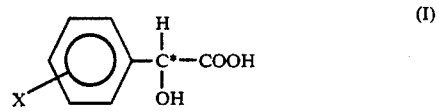

wherein X represents a hydrogen atom, a halogen atom, a hydroxyl group, an aliphatic saturated alkyl group having from 1 to 3 carbon atoms, an aliphatic saturated alkoxy group having from 1 to 3 carbon atoms, a thioalkyl group, an amino group, a nitro group, a phenyl group, or a phenoxy group, which is bonded to the o-, m-, or p-position; which comprises subjecting the following compound (i) or (ii)

(i) R,S-mandelonitrile or a derivative thereof represented by formula (II):

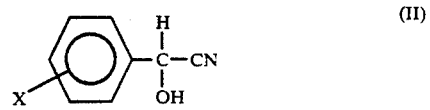

wherein X is as defined above, or
(ii) a mixture of prussic acid and benzaldehyde or a derivative of benzaldehyde represented by formula (III):

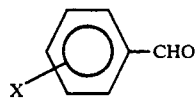
(III)

wherein X is as defined above; to the action of a microorganism selected from the group consisting of the genus Aureobacterium, Pseudomonas, Caseobacter, Alcaligenes, Acinetobacter, Brevibacterium, Nocardia, and Bacillus or treated cells thereof, which said microorganism is capable of stereospecifically hydrolyzing a nitrile group of the R,S-mandelonitrile or a derivative thereof represented by formula II; in a neutral or basic aqueous reaction system to produce the R(−)-mandelic acid.

The present invention is based on the fact that R,S-mandelonitrile and its derivative as represented by formula (II) readies a dissociation equilibrium in a neutral to basic aqueous medium with prussic acid and benzaldehyde or its derivative as represented by formula (III); and thus, is easily racemized and the action of a microorganism capable of asymmetrically hydrolyzing R,S-mandelonitrile or a derivative thereof in conjunction with the above-described racemization system to predominantly produce R(−)-prodelic acid or a derivative thereof represented by formula (I) is achieved.

DETAILED DESCRIPTION OF THE INVENTION

Specific examples of microorganisms which can be used in the present invention include *Aureobacterium testaceum* (IAM 1561), Pseudomonas sp. BC13-2 (FERM BP-3319), Pseudomonas sp. BC15-2 (FERM BP-3320), Caseobacter sp. BC4 (FERM BP-3316), Caseobacter sp. BC23 (FERM P-11261), Alcaligenes sp. BC12-2 (FERM P-11263), Alcaligenes sp. BC20 (FERM P-11264), Alcaligenes sp. BC35-2 (FERM BP-3318), Alcaligenes sp. BC24 (FERM P-12063), Acinetobacter sp. BC9-2 (FERM BP-3317), Brevibacterium acetylicum (*IAM* 1790), *Nocardia asteroides* (IFO 3384), and *Bacillus subtilis* (ATCC 21697), and variants of these strains.

Of these microorganisms, *Aureobacterium testaceum* (IAM 1561), *Brevibacterium acetylicum* (IAM 1790), *Nocardia asteroides* (IFO 3384), and *Bacillus subtilis* (ATCC 21697) are known strains that are readily available from the Institute of Applied Microbiology, The University of Tokyo (IAM); the Institute for Fermentation, Osaka (IFO); or the American Type Culture Collection (ATCC) under the deposit numbers listed above.

Pseudomonas sp. BC13-2 and BC15-2; Caseobacter sp. BC4 and BC23; Alcaligenes sp. BC12-2, BC20, BC35-2 and BC24; and Acinetobacter sp. BC9-2 are new strains isolated by the inventors from the soil which have been deposited with Fermentation Research Institute, Agency of Industrial Science & Technology, 1-3, Higashi 1-chrome, Tusukuba-shi, Ibaraki, Japan under the deposit numbers (FERM Nos.) listed above. The morphological and physiological properties of these new strains are described below.

| | |
|---|---|
| Pseudomonas sp. BC13-2 and BC15-2 Strains: | |
| Shape: | bacillus |
| Gram staining: | − |
| Spore: | + |
| Mobility: | + |
| Flagella | polar |
| Oxidase: | + |
| Catalase: | + |
| O-F test: | O |
| Caseobactor sp. BC4 and BC23 Strains: | |
| Shape: | polymorphic bacillus |
| Gram staining: | + |
| Spore: | − |
| Mobility: | − |
| Oxidase: | − |
| Catalase: | + |
| Rod-coccus cycle: | + |
| Extension of periphery of colony: | not observed |
| Growth under anaerobic condition: | − |
| Diamino acid of cell wall: | meso-diaminopimelic acid |
| Glycolyl test: | − (acetyl type) |
| Sugar composition of cell wall: | |
| Arabinose: | + |
| Galactose: | + |
| Existence of quinone: | MK-8 (H$_2$) |
| Alcaligenes sp. BC12-2, BC20, BC35-2 and BC24 Strains: | |
| Shape: | bacillus |
| Gram staining: | − |
| Spore: | − |
| Mobility: | + |
| Flagella: | peritrichous |
| Oxidase: | + |
| Catalase: | + |
| O-F test: | alkalization |
| 3-Ketolactose production: | − |
| Existence of quinone: | Q-8 |
| Acinetobacter sp. BC9-2 Strain: | |
| Shape: | bacillus |
| Gram staining: | − |
| Spore: | − |
| Mobility: | − |
| Oxidase: | − |
| Catalase: | + |
| O-F test: | − |

The above-described taxonomical properties were classified according to *Bergey's Manual of Systematic Bacteriology* (1986) and, as a result, BC13-2 and BC15-2 strains were identified to belong to the genus Pseudomonas; BC4 and BC23 strains the genus Caseobacter; BC12-2, BC20, BC35-2 and BC24 strains the genus Alcaligenes; and BC9-2 strain the genus Acinetobacter, respectively.

Cultivation of these microorganisms is carried out using a media containing assimilable carbon sources (e.g., glycerol, glucose, and saccharose), assimilable nitrogen sources (e.g., urea, ammonium sulfate, and ammonium nitrate), and inorganic nutrients essential for growth (e.g., magnesium chloride, calcium chloride, and iron chloride). The media may also further contain natural media, such as yeast extract, meat extract, and molasses.

In order to obtain increased enzyme activity, an enzyme inducer can be added to the culture medium in the initial or middle stage of cultivation at a concentration that does not greatly inhibit growth. Suitable enzyme inducers include nitriles (e.g., cinnamonitrile, benzyl cyanide, isobutyronitrile, benzonitrile, 1-cyclohexenyl acetonitrile, β-phenylpropionitrile, 4-cyanopyridine, phenylsulfonyl acetonitrile, and γ-butyronitrile) and amides (e.g., isobutylamide, 4-pyridinecarboxylic acid amide, and phenylacetamide).

Culturing is conducted aerobically at a pH of from 4 to 10 at 5° to 50° C. for a period of about 1 to 14 days until the maximum activity is reached.

The asymmetric hydrolysis reaction of R,S-mandelonitrile and its derivatives according to the claimed invention can be carried out by bringing harvested microbial cells that are whole or that have been treated (e.g., ruptured cells, crude or purified enzyme, or immobilized microbial cells or enzyme) together with R,S-mandelonitrile or a derivative thereof or a mixture of prussic acid and benzaldehyde or a derivative of benzaldehyde in an aqueous medium, e.g., water and a buffer solution.

It is essentially required that the reaction system be maintained at about a neutral or basic condition in order to racemize optically active mandelonitrile or a derivative thereof as stated above. That is, the pH of the reaction system should be kept within a range of from 4 to 11, and preferably from 6 to 10. Other reaction conditions, as follows, vary depending on the sensitivity of the enzyme produced by the microorganism to prussic acid and benzaldehyde or a derivative of benzaldehyde.

The concentrations of mandelonitrile or its derivative; benzaldehyde and its derivative; and prussic acid in the reaction system usually range from 0.1 to 10% by weight (preferably from 0.2 to 5.0% by weight); from 0.1 to 10% by weight (preferably from 0.2 to 5.0% by weight); and from 0.1 to 1.0% by weight (preferably from 0.1 to 0.5% by weight); respectively. The microorganism is usually used in an amount of from 0.01 to 5.0% by weight on a dry basis based on the weight of the substrate, such as mandelonitrile or a derivative thereof. The reaction is usually conducted at a temperature of from 0° to 50° C., and preferably from 10° to 30° C., for a period of from 0.1 to 100 hours.

If an R,S-mandelonitrile derivative or benzaldehyde derivative has a very low solubility in an aqueous medium, the reaction may proceed even in a homogeneous phase. However, it is preferable for efficiency to add a surface active agent (e.g., Triton X-100 and Tween 60) at a concentration of from 0.1 to 10% by weight, or to add ethanol or dimethyl sulfoxide (hereinafter abbreviated as DMSO) as an auxiliary solvent.

Thus, R,S-mandelonitrile or its derivative or a mixture of prussic acid and benzaldehyde or a derivative of benzaldehyde is converted to an optically active mandelic acid or a derivative thereof at a high yield through the asymmetric hydrolysis of a nitrile by the action of the microorganism in conjunction with the racemization that takes place in a dissociation equilibrium reaction in an aqueous medium.

The reaction product can be isolated from the reaction mixture by removing the insoluble matter including microbial cells and then utilizing any known purification means, such as concentration, ion exchange, electrodialysis, extraction, and crystallization.

According to the process of the present invention, R(−)-mandelic acid or a derivative thereof can be obtained directly from racemic R,S-mandelonitrile or a derivative thereof or prussic acid and benzaldehyde or a derivative of benzaldehyde in a predominant proportion (50 to 100%). Because it is possible to stoichiometrically convert all the starting material(s) to R(−)-mandelic acid or a derivative thereof, the present invention provides an extremely efficient process for producing R(−)-mandelic acid or a derivative thereof.

The present invention is now illustrated in greater detail with reference to the following Examples. However it is not intended that the present invention be limited to these Examples.

EXAMPLE 1

(1) Culturing

Each of the microorganisms shown in Table 1 below was inoculated on plated medium of the following composition and cultured at 30° C. for 72 hours.

| Medium Composition: | |
|---|---|
| Glycerol | 2.0 w/v % |
| Yeast extract | 0.30 w/v % |
| Potassium primary phosphate | 0.68 w/v % |
| Sodium secondary phosphate | 0.71 w/v % |
| Sodium sulfate | 0.28 w/v % |
| Magnesium chloride | 0.04 w/v % |
| Calcium chloride | 0.004 w/v % |
| Manganese sulfate | $4 \times 10^{-4}$ w/v % |
| Iron chloride | $6 \times 10^{-5}$ w/v % |
| Zinc sulfate | $3 \times 10^{-5}$ w/v % |
| Agar | 1.80 w/v % |
| Benzyl cyanide | 0.02 w/v % |
| pH = 7.5 | |

(2) Asymmetric Hydrolysis of Mandelonitrile

Microbial cells harvested from the plate culture were washed with a 50 mM phosphoric acid buffer solution (pH=7.5) and suspended in 10 ml of the same buffer solution to prepare a resting cell suspension at a cell concentration having an optical density at 630 nm ($OD_{630}$) of from 1 to 50. To the cell suspension was added mandelonitrile to a concentration of 0.2 w/v %, and the system was allowed to react at 30° C. for 16 to 24 hours. Analysis of the reaction mixture by liquid chromatography (Shiseido ODS column); revealed the production of mandelic acid and ammonia. Further, analysis by means of a chiral cell for optical resolution("CHIRALPAK WH" column) revealed that the produced R(−)-mandelic acid had a high optical purity.

TABLE 1

| | Produced Mandelic Acid | |
|---|---|---|
| Strain | Yield (%) | Optical Purity (% ee) |
| BC13-2 | 97.4 | 93.4 |
| BC12-2 | 88.9 | 100 |
| BC20 | 35.7 | 100 |
| BC35-2 | 89.1 | 100 |
| BC24 | 98.0 | 100 |
| BC9-2 | 25.2 | 100 |
| BC4 | 61.2 | 100 |
| BC23 | 36.8 | 100 |

EXAMPLE 2

(1) Culturing

Alcaligenes sp. BC12-2 was cultured in Medium A shown below at 30° C. for 72 hours. The resulting microbial cells were successively cultured in Medium B shown below at 30° C. for 48 hours.

| Medium A Composition: | |
|---|---|
| Glycerol | 2.0 w/v % |
| Yeast extract | 0.30 w/v % |
| Potassium primary phosphate | 0.68 w/v % |
| Sodium secondary phosphate | 0.71 w/v % |
| Sodium sulfate | 0.28 w/v % |
| Magnesium chloride | 0.04 w/v % |
| Calcium chloride | 0.004 w/v % |
| Manganese sulfate | $4 \times 10^{-4}$ w/v % |
| Iron chloride | $6 \times 10^{-5}$ w/v % |
| Zinc sulfate | $3 \times 10^{-5}$ w/v % |
| pH = 7.5 | |

Medium B Composition

Prepared by adding benzyl cyanide to Medium A in a concentration of 0.02 w/v %.

(2) Asymmetric Hydrolysis of Mandelonitrile

Microbial cells were harvested and washed with a 50 mM phosphoric acid buffer solution (pH=7.5) and suspended in 100 ml of the same buffer solution to prepare a resting cell suspension ($OD_{630}$=50.48). To the cell suspension 0.2 g of mandelonitrile. The system was allowed to react at 30° C. In one hour from the start of the reaction, it was found that mandelonitrile was completely converted to R(—)-mandelic acid and ammonia almost quantitatively. A 0.2 g portion of mandelonitrile was added to the reaction mixture every hour to continue the reaction for an overall reaction time of 14 hours. Analysis of the reaction mixture by liquid chromatography (Shiseido ODS column) revealed that 2.73 w/v % (conversion yield: 88.93%) of ammonium R(—)-mandelate was produced and accumulated in 14 hours from the start of the reaction. The reaction mixture was freed of microbial cells by centrifugation, adjusted to a pH of 2 with an acid, and extracted with ethyl acetate to obtain a mandelic acid extract. The extract was dried over anhydrous sodium sulfate and freed of the organic solvent to obtain a crude crystal. Recrystallization of the crude crystal from ethyl acetate gave a white crystal powder.

Each resulting crystal and, for reference, standard mandelic acid was dissolved in 6N aqueous ammonia and messed up with distilled water to form ammonium mandelate at a concentration of 1.0 w/v%. Optical rotation of the thus formed ammonium mandelate was determined.

The results of analyses are shown in Table 2 below.

TABLE 2

| Sample | Purity (%) | Optical Purity (% ee) | Ammonium Mandelate $[\alpha]_D^{20}$ |
|---|---|---|---|
| Example 2 (BC12-2) | 101.9 | 100 | —116.5 |
| Standard Sample | 100 | 100 | —116.5 |

EXAMPLE 3

(1) Culturing

Alcaligenes sp. BC35-2 was cultured under the same conditions as in Example 2.

(2) Asymmetric Hydrolysis of Mandelonitrile

Microbial cells were harvested, and a cell suspension having a cell concentration of $OD_{630}$=59.50 was prepared and allowed to react in the same manner as in Example 1. Within 14 hours from the start of the reaction, the substrate completely disappeared. In 42 hours from the start of the reaction, the ammonium mandelate content accumulated in the reaction mixture was found to be 3.79 w/v % (conversion yield: 89.09%).

The reaction mixture was worked-up in the same manner as in Example 2. The results of analyses are shown in Table 3 below.

TABLE 3

| Sample | (%) | Optical Purity (% ee) | Ammonium Mandelate $[\alpha]_D^{20}$ |
|---|---|---|---|
| Example 3 (BC35-2) | 99.2 | 100 | —114.0 |
| Standard Sample | 100 | 100 | —116.5 |

EXAMPLE 4

(1) Culturing

Pseudomonas sp. BC13-2 was cultured under the same conditions as in Example 2.

Production of R(—)-Mandelic Acid from Benzaldehyde and Prussic Acid

Microbial cells were harvested as described in Example 1, and suspended in 100 ml of a 50 mM phosphoric acid buffer solution (pH=7.5) to prepare a resting cell suspension ($OD_{630}$=50.5). To these cell suspensions were added prussic acid and benzaldehyde each to the final concentration of 15 mM, and the system was allowed to react at 30° C. In one hour from the start of the reaction, it was found that the mandelonitrile produced by dissociation equilibrium and benzaldehyde completely disappeared and R(—)-mandelic acid and ammonia were quantitatively produced. Then, 15 mM each of benzaldehyde and prussic acid was successively added to the reaction system every hour to continue the reaction. After 14 hours, 2.6 w/v % of ammonium R(—)-mandelate was accumulated (conversion yield: 84.7%). The optical purity was found to be 100%ee determined in the same manner as in Example 2.

EXAMPLE 5

(1) Culturing

A loopful of each of the microorganisms shown in Table 4 below was taken from a slant medium and inoculated on a plate medium having the following composition and aerobically cultured at 30° C. for 72 hours.

| Medium Composition: | |
|---|---|
| Glycerol | 0.5 w/v % |
| Yeast extract | 0.02 w/v % |
| Potassium primary phosphate | 0.68 w/v % |
| Sodium secondary phosphate | 0.71 w/v % |
| Sodium sulfate | 0.28 w/v % |
| Magnesium chloride | 0.04 w/v % |
| Calcium chloride | 0.004 w/v % |
| Manganese sulfate | $4 \times 10^{-4}$ w/v % |
| Iron chloride | $6 \times 10^{-5}$ w/v % |
| Zinc sulfate | $3 \times 10^{-5}$ w/v % |
| Agar | 1.8 w/v % |
| Benzyl cyanide | 0.05 w/v % |
| pH = 7.5 | |

(2) Production of R(−)-Mandelic Acid from R,S-Mandelonitrile

Microbial cells harvested from the plates were centrifugally washed three times with a 50 mM phosphoric acid buffer solution (pH=7.5). The sedimented cells were resuspended in 1.5 ml of the same buffer solution, and racemic mandelonitrile was added thereto to a final concentration of 14 mM. This mixture was allowed to react at 30° C. for 24 hours while shaking. After the reaction, the microbial cells were separated by centrifugation, and the mandelic acid in the supernatant was determined by liquid chromatography (column: "SHODEX ODS F511A"; carrier: 0.2 M $H_3PO_4$ acetonitrile=4:1; monitor: 208 nm), and the optical purity of the produced mandelic acid was determined by liquid chromatography (column: "CHIRALPAK WH"; carrier: 0.25 mM copper sulfate aqueous solution; monitor: 208 nm).

COMPARATIVE EXAMPLE 1

For comparison, *Alcaligenes faecalis* (ATCC 8750) described in JP-A-2-84198 was cultured in the same manner as described in Example 5, above; and a hydrolysis reaction was carried out using the resulting microbial cells in the same manner as described in Example 5 above.

Results of the analyses are shown in Table 4.

TABLE 4

| Example No. | Strain | Culturing Time (hr) | Cell Concn. ($OD_{630}$) | Yield (%) | Optical Purity (% ee) |
|---|---|---|---|---|---|
| Example 5 | IFO 3384 | 72 | 50 | 89.4 | 92.3 |
| | ATCC 21697 | 144 | 40 | 100 | 98.0 |
| | IAM 1561 | 72 | 48 | 94.1 | 97.3 |
| | IAM 1790 | 72 | 2 | 61.2 | 50.6 |
| Comparative Example 1 | ATCC 8750 | 72 | 40 | 30.2 | 85.0 |
| Reference Example* | ATCC 8750 | 48 | 53 | 0 | — |

Note: In the Reference Example, culturing conditions were in accordance with JP-A-2-84198, and the amount of microbial cells used for the reaction was about 30 times that used in the publication.

EXAMPLE 6

(1) Culturing

*Aureobacterium testaceum* (IAM 1561) was cultured under the conditions described in Example 5.

(2) Production of R(−)-Mandelic Acid from Benzaldehyde and Prussic Acid

Microbial cells harvested from the culture were washed in the manner described in Example 5 and suspended in 1.5 ml of a 50 mM phosphoric acid buffer solution (pH=7.5) to prepare a resting cell suspension ($OD_{630}$=40). To the suspension were added benzaldehyde and prussic acid each to a final concentration of 15 mM. The mixture was allowed to react at 433 30° C. for 24 hours while shaking. After the reaction, the microbial cells were separated by centrifugation, and the content and optical purity of mandelic acid accumulated in the supernatant determined in the manner described in Example 5. As a result, it was found that 13.5 mM of R(−)-mandelic acid having an optical purity of 97.1%ee had accumulated for a conversion yield of 90.0%.

EXAMPLE 7

(1) Culturing

*Aureobacterium testaceum* (IAM 1561) was aerobically cultured in Medium A shown below at 30° C. for 72 hours. The resulting microbial cells were successively cultured in Medium B shown below at 30° C. for 90 hours.

| Medium A Composition: | |
|---|---|
| Glycerol | 20 g/l |
| Yeast extract | 6 g/l |
| Potassium primary phosphate | 6.8 g/l |
| Sodium secondary phosphate | 7.1 g/l |
| Sodium sulfate | 2.8 g/l |
| Magnesium chloride | 0.4 g/l |
| Calcium chloride | $4 \times 10^{-2}$ g/l |
| Manganese sulfate | $4 \times 10^{-3}$ g/l |
| Iron chloride | $6 \times 10^{-4}$ g/l |
| Zinc sulfate | $3 \times 10^{-4}$ g/l |
| Distilled water | 1000 ml |
| pH = 7.5 | |

Medium B Composition

Medium B was prepared by adding 1-cyclohexenyl acetonitrile to Medium A in a concentration of 0.02 w/v %.

(2) Production of R(−)-2-Chloromandelic Acid from R,S-2-Chloromandelonitrile Microbial cells harvested from the culture were washed with a 50 mM phosphoric acid buffer solution (pH=7.5) and suspended in 10 ml of the same buffer solution to prepare a resting cell suspension ($OD_{630}$26). To the cell suspension was added 14.5 mM of R,S-2-chloromandelonitrile. This mixture was allowed to react at 30° C. for 3 hours, after which time the microbial cells were removed by centrifugal separation. Analysis of the supernatant by liquid chromatography (column: "SHODEX ODS F511A"; carrier: 0.2 M $H_3PO_4$:acetonitrile=4:1; monitor: 208 nm) revealed that 12.9 mM (yield: 89%) of 2-chloromandelic acid was produced. Further, optical purity of this 2-chloromandelic acid was found to be 98.2%ee as analyzed by means of a chiral cell for optical resolution (column: "CHIRALPAK WH").

EXAMPLE 8

(1) Culturing

*Aureobacterium testaceum* (IAM 1561) was cultured under the conditions described in Example 7.

(2) Production of R(−)-2-Chloromandelic Acid from 2-Chlorobenzaldehyde and Prussic Acid Microbial cells were harvested from culture, and a resting cell suspension ($OD_{630}$=26) prepared in the manner described in Example 7. To the cell suspension were added 2-chlorobenzaldehyde and prussic acid each to a final concentration of 14 mM. This mixture was allowing to react at 30° C. for 3 hours while shaking, after which time the microbial cells were removed by centrifugation and analyzed in the same manner as described in Example 7. It was found as a result that 13.2 mM (yield: 94.3%) of 2-chloromandelic acid was produced and the optical purity of the product was 98.1%ee.

EXAMPLE 9

(1) Culturing

*Aureobacterium testaceum* (IAM 1561) was cultured under the conditions described in Example 7.

(2) Production of R(−)-4-Phenylmandelic Acid from 4-Phenylbenzaldehyde and Prussic Acid A resting cell suspension (OD$_{630}$=58.1) was prepared using microbial cells collected from culture in the manner described in Example 7. To the cell suspension were added 4-phenylbenzaldehyde, prussic acid, and DMSO to a concentration of 1.0 mM, 1.0 mM, and 1.4 M (10 wt %), respectively. This mixture was allowed to react at 30° C. for 23 hours, after which time the microbial cells were removed and the supernatant analyzed as described in Example 7. It was found as a result that 0.71 mM (yield: 71%) of 4-phenylmandelic acid was produced and the optical purity of the product was 76.7%ee.

EXAMPLE 10

(1) Culturing

*Aureobacterium testaceum* (IAM 1561) was cultured under the conditions described in Example 7.

(2) Production of R(−)-Mandelic Acid Derivatives

A resting cell suspension (OD$_{630}$=5 to 79.3) was prepared using microbial cells harvested from culture as described in Example 7. To the suspension were added an R,S-mandelonitrile derivative or prussic acid and a benzaldehyde derivative as shown in Table 5 below. This mixture was allowed to react at 30° C. for 2 to 20 hours while shaking, after which time the microbial cells were removed and the reaction yield and optical purity of the product determined as described in Example 7. The results obtained are shown in Table 5.

TABLE 5

| Substrate | Amount of Substrate (mM) | Amount Microbial Cells (OD$_{630}$) | Reaction Time (hr) | R(−)-Mandelic Acid Derivative X | Amount of Production (mM) | Yield (%) | Optical Purity (% ee) |
|---|---|---|---|---|---|---|---|
| 3-Chloromandelonitrile | 11.0 | 26.0 | 2 | 3 Cl— | 9.3 | 84.5 | 95.6 |
| 4-Chloromandelonitrile | 13.9 | 26.0 | 3 | 4 Cl— | 12.7 | 91.4 | 100 |
| 4-Bromomandelonitrile | 4.1 | 5.0 | 16 | 4-Br— | 3.3 | 80.5 | 100 |
| 4-Fluoromandelonitrile | 4.0 | 40.0 | 20 | 4 F— | 3.5 | 87.5 | 96.0 |
| 4-Hydroxybenzaldehyde | 7.4 | 5.0 | 17 | 4 HO— | 7.5 | 101.4 | 97.6 |
| Prussic acid | 8.6 | | | | | | |
| 4-Methylbenzaldehyde | 8.3 | 5.0 | 17 | 4 CH$_3$— | 8.0 | 96.4 | 100 |
| Prussic acid | 10.3 | | | | | | |
| 4-Methoxybenzaldehyde | 9.6 | 5.0 | 17 | 4 CH$_3$O— | 6.7 | 69.8 | 100 |
| Prussic acid | 10.5 | | | | | | |
| 4-Methylthiomandelonitrile | 4.5 | 26.0 | 20 | 4 CH$_3$S— | 3.1 | 68.9 | 93.0 |
| 4-Isopropylmandelonitrile (added with 10% DMSO) | 0.8 | 61.6 | 18 | 4 (CH$_3$)$_2$CH— | 0.6 | 75.0 | 63.0 |
| 4-Aminomandelonitrile | 5.5 | 26.0 | 20 | 4 H$_2$N— | 4.3 | 78.2 | 87.0 |
| 4-Nitromandelonitrile | 4.0 | 26.0 | 20 | 4 O$_2$N— | 2.6 | 65.0 | 83.0 |
| 3-Phenoxymandelonitrile (added with 10% DMSO) | 1.7 | 79.3 | 20 | 3 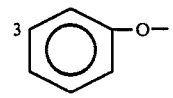—O— | 1.2 | 70.6 | 29.0 |

EXAMPLE 11

(1) Culturing

*Pseudomonas* sp. BC13-2 was cultured under the conditions described in Example 7.

(2) Production of R(−)-Mandelic Acid Derivatives

A resting cell suspension (OD$_{630}$=9 to 99.7) was prepared using microbial cells collected from culture in the manner described in Example 10. To the suspension were added an R,S-mandelonitrile derivative or prussic acid a benzaldehyde derivative as shown in Table 6 below. Each mixtures was allowed to react at 30° C. for 4 to 24 hours while shaking, after which time the microbial cells were removed and the reaction yield and optical purity of the product determined as in described Example 7. The results obtained are shown in Table 6.

TABLE 6

| Substrate | Amount of Substrate (mM) | Amount Microbial Cells (OD$_{630}$) | Reaction Time (hr) | R(−)-Mandelic Acid Derivative X | Amount of Production (mM) | Yield (%) | Optical Purity (% ee) |
|---|---|---|---|---|---|---|---|
| 3-Chloromandelonitrile | 11.0 | 26.0 | 2 | 3 Cl— | 9.3 | 84.5 | 95.6 |
| 2-Chloromandelonitrile | 14.5 | 24.0 | 4 | 2 Cl— | 13.5 | 93.1 | 58.6 |

TABLE 6-continued

| Substrate | Amount of Substrate (mM) | Amount Microbial Cells (OD$_{630}$) | Reaction Time (hr) | R(−)-Mandelic Acid Derivative | | | |
|---|---|---|---|---|---|---|---|
| | | | | X | Amount of Production (mM) | Yield (%) | Optical Purity (% ee) |
| 3-Chloromandelonitrile | 11.0 | 24.0 | 4 | 3 Cl— | 9.1 | 82.7 | 100 |
| 4-Chloromandelonitrile | 13.9 | 24.0 | 24 | 4 Cl— | 9.0 | 64.7 | 100 |
| 4-Hydroxybenzaldehyde | 7.4 | 9.0 | 17 | 4 HO— | 7.3 | 98.6 | 100 |
| Prussic acid | 8.0 | | | | | | |
| 4-Methylbenzaldehyde | 8.3 | 24.0 | 17 | 4 CH$_3$— | 8.0 | 96.4 | 100 |
| Prussic acid | 10.3 | | | | | | |
| 4-Methoxybenzaldehyde | 4.8 | 52.7 | 17 | 4 CH$_3$O— | 3.7 | 77.1 | 100 |
| Prussic acid | 5.1 | | | | | | |
| 4-Isopropylmandelo-nitrile (added with 10% DMSO) | 1.3 | 99.7 | 20 | 4 (CH$_3$)$_2$CH— | 0.8 | 61.5 | 62.0 |
| 3-Phenoxymandelo-nitrile (added with 10% DMSO) | 2.5 | 99.7 | 23 | 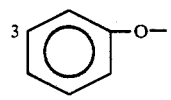 | 1.5 | 60.0 | 90.7 |

EXAMPLE 12

(1) Culturing

Caseobacter sp. BC4 was cultured under the same conditions described in Example 7.

(2) Production of R(−)-Mandelic Acid Derivatives

A resting cell suspension (OD$_{630}$=13 or 39) was prepared using microbial cells harvested from culture as described in Example 10. To the suspension were added an R,S-mandelonitrile derivative or prussic acid and a benzaldehyde derivative as shown in Table 7 below. Each mixture was allowed to react at 30° C. for 2 to 20 hours while shaking, after which time the microbial cells were removed and the reaction yield and optical purity of the product determined as described in Example 7. The results obtained are shown in Table 7.

EXAMPLE 13

(1) Culturing

Alcaligenes sp. BC35-2 was cultured under the conditions described in Example 7.

(2) Production of R(−)-Mandelic Acid Derivatives

A resting cell suspension (OD$_{630}$=14.8 or 28) was prepared using microbial cells harvested from culture in the manner described in Example 10. To the suspension were added an R,S-mandelonitrile derivative or prussic acid and a benzaldehyde derivative as shown in Table 8 below. Each mixture was allowed to react at 30° C. for 2 to 17 hours while shaking, after which time the microbial cells were removed and the reaction yield and optical purity of the product determined as described in Example 7. The results obtained are shown in Table 8.

TABLE 7

| Substrate | Amount of Substrate (mM) | Amount of Microbial Cells (OD$_{630}$) | Reaction Time (hr) | R(−)-Mandelic Acid Derivative | | | |
|---|---|---|---|---|---|---|---|
| | | | | X | Amount of Production (mM) | Yield (%) | Optical Purity (% ee) |
| 2-Chloromandelonitrile | 14.5 | 39.0 | 2 | 2 Cl— | 9.6 | 66.2 | 100 |
| 3-Chloromandelonitrile | 11.0 | 39.0 | 2 | 3 Cl— | 9.3 | 84.5 | 99.6 |
| 4-Chloromandelonitrile | 13.9 | 39.0 | 3 | 4 Cl— | 12.6 | 90.6 | 100 |
| 4-Bromomandelonitrile | 4.1 | 13.0 | 16 | 4 Br— | 2.9 | 70.7 | 100 |
| 4-Hydroxybenzaldehyde | 7.4 | 13.0 | 17 | 4 HO— | 6.3 | 85.1 | 94.8 |
| Prussic acid | 8.0 | | | | | | |
| 4-Methylbenzaldehyde | 8.3 | 13.0 | 17 | 4 CH$_3$— | 8.3 | 100 | 100 |
| Prussic acid | 10.3 | | | | | | |
| 4-Methoxybenzaldehyde | 9.6 | 13.0 | 20 | 4 CH$_3$O— | 7.3 | 76.0 | 100 |
| Prussic acid | 10.5 | | | | | | |

TABLE 8

| Substrate | Amount of Substrate (mM) | Amount of Microbial Cells (OD$_{630}$) | Reaction Time (hr) | R(−)-Mandelic Acid Derivative | | | |
|---|---|---|---|---|---|---|---|
| | | | | X | Amount of Production (mM) | Yield (%) | Optical Purity (% ee) |
| 2-Chloromandelonitrile | 14.5 | 28.0 | 2 | 2 Cl— | 10.3 | 71.0 | 93.1 |
| 3-Chloromandelonitrile | 11.0 | 28.0 | 2 | 3 Cl— | 9.3 | 84.5 | 84.8 |
| 4-Chloromandelonitrile | 13.9 | 28.0 | 2 | 4 Cl— | 8.7 | 62.6 | 98.3 |

TABLE 8-continued

| Substrate | Amount of Substrate (mM) | Amount of Microbial Cells (OD$_{630}$) | R(−)-Mandelic Acid Derivative | | | |
|---|---|---|---|---|---|---|
| | | | Reaction Time (hr) | X | Amount of Production (mM) | Yield (%) | Optical Purity (% ee) |
| 4-Bromomandelonitrile | 4.1 | 14.8 | 16 | 4 Br— | 3.5 | 85.4 | 100 |
| 4-Hydroxybenzaldehyde | 7.4 | 14.8 | 17 | 4 HO— | 7.4 | 100 | 100 |
| Prussic acid | 7.6 | | | | | | |
| 4-Methylbenzaldehyde | 8.3 | 14.8 | 17 | 4 CH$_3$— | 8.3 | 100 | 100 |
| Prussic acid | 10.3 | | | | | | |
| 4-Methoxybenzaldehyde | 9.6 | 14.8 | 17 | 4 CH$_3$O— | 9.6 | 100 | 100 |
| Prussic acid | 10.8 | | | | | | |

EXAMPLE 14

(1) Culturing

Acinetobacter sp. BC9-2 was cultured under the same described in Example 7.

(2) Production of R(−)-Mandelic Acid Derivatives

A resting cell suspension (OD$_{630}$=7.1 to 28.2) was prepared using microbial cells harvested from culture as described in Example 10. To the suspension were added an R,S-mandelonitrile derivative or prussic acid and a substituted benzaldehyde derivative as shown in Table 9 below. Each mixture was allowed to react at 30° C. for 9 to 20 hours while shaking, after which time the microbial cells were removed and the reaction yield and the optical purity of the product determined as described in Example 7. The results obtained are shown in Table 9.

| Medium Composition: | |
|---|---|
| Glycerol | 5 g/l |
| Yeast extract | 0.2 g/l |
| Potassium primary phosphate | 6.8 g/l |
| Sodium secondary phosphate | 7.1 g/l |
| Sodium sulfate | 2.8 g/l |
| Magnesium chloride | 0.4 g/l |
| Calcium chloride | 4 × 10$^{-2}$ g/l |
| Manganese sulfate | 4 × 10$^{-3}$ g/l |
| Iron chloride | 6 × 10$^{-4}$ g/l |
| Zinc sulfate | 3 × 10$^{-4}$ g/l |
| Benzyl cyanide | 0.5 g/l |
| Agar | 18 g/l |
| Distilled water | 1000 ml |
| pH = 7.5 | |

(2) Production of R(−)-2-Chloromandelic Acid

Microbial cells harvested from the culture were

TABLE 9

| Substrate | Amount of Substrate (mM) | Amount of Microbial Cells (OD$_{630}$) | R(−)-Mandelic Acid Derivative | | | | |
|---|---|---|---|---|---|---|---|
| | | | Reaction Time (hr) | X | Amount of Production (mM) | Yield (%) | Optical Purity (% ee) |
| 2-Chloromandelonitrile | 11.0 | 22.0 | 20 | 3 Cl— | 7.3 | 66.3 | 100 |
| 4-Chloromandelonitrile | 13.9 | 22.0 | 9 | 4 Cl— | 11.3 | 81.3 | 100 |
| 4-Bromomandelonitrile | 4.1 | 7.1 | 16 | 4 Br— | 3.6 | 87.8 | 100 |
| 4-Hydroxybenzaldehyde | 7.4 | 7.1 | 16 | 4 HO— | 5.6 | 78.9 | 91.6 |
| Prussic acid | 8.6 | | | | | | |
| 4-Methylbenzaldehyde | 8.3 | 28.2 | 17 | 4 CH$_3$— | 7.0 | 84.3 | 100 |
| Prussic acid | 9.3 | | | | | | |
| 4-Methoxybenzaldehyde | 0.6 | 7.1 | 17 | 4 CH$_3$O— | 0.4 | 66.7 | 100 |
| Prussic acid | 0.7 | | | | | | |

EXAMPLE 15

(1) Culturing

Brevibacterium acetylicum (IAM 1790) was cultured in a medium having the following composition at 30° C. for 72 hours.

washed once with a 50 mM phosphoric acid buffer solution (pH=7.5) and suspended in 10 ml of the same buffer solution to prepare a resting cell suspension (OD$_{630}$=30). To the cell suspension were added a benzaldehyde derivative and prussic acid as shown in Table 10 below, and the system was allowed to react at 30° C. for 20 hours with shaking. The microbial cells were removed and the supernatant analyzed to determine the yield and optical purity of the product as in Example 7. The results obtained are shown in Table 10.

TABLE 10

| Substrate | Amount of Substrate (mM) | Amount of Microbial Cells (OD$_{630}$) | R(−)-Mandelic Acid Derivative | | | | |
|---|---|---|---|---|---|---|---|
| | | | Reaction Time (hr) | X | Amount of Production (mM) | Yield (%) | Optical Purity (% ee) |
| 4-Hydroxybenzaldehyde | 4.6 | 30.0 | 20 | 4 HO— | 2.9 | 63.0 | 95.0 |

TABLE 10-continued

| Substrate | Amount of Substrate (mM) | Amount of Microbial Cells (OD$_{630}$) | Reaction Time (hr) | R(−)-Mandelic Acid Derivative | | | |
|---|---|---|---|---|---|---|---|
| | | | | X | Amount of Production (mM) | Yield (%) | Optical Purity (% ee) |
| Prussic acid | 4.7 | | | | | | |
| 4-Methylbenzaldehyde | 8.3 | 30.0 | 20 | 4 CH$_3$— | 6.0 | 72.3 | 100 |
| Prussic acid | 8.3 | | | | | | |

EXAMPLE 16

(1) Culturing

*Nocardia asteroides* (IFO 3384) was cultured under the conditions described in Example 15.

(2) Production of R(−)-Mandelic Acid Derivatives

A resting cell suspension (OD$_{630}$=30) was prepared using microbial cells harvested from culture in the manner described in Example 15. To the suspension were added a benzaldehyde derivative and prussic acid as shown in Table 11. This mixture was allowed to react as described in Example 15. The results of analyses of the product are shown in Table 11.

TABLE 11

| Substrate | Amount of Substrate (mM) | Amount of Microbial Cells (OD$_{630}$) | Reaction Time (hr) | R(−)-Mandelic Acid Derivative | | | |
|---|---|---|---|---|---|---|---|
| | | | | X | Amount of Production (mM) | Yield (%) | Optical Purity (% ee) |
| 4-Hydroxybenzaldehyde | 4.6 | 30.0 | 20 | 4 HO— | 3.9 | 84.8 | 96.2 |
| Prussic acid | 4.7 | | | | | | |
| 4-Methylbenzladehyde | 8.3 | 30.0 | 20 | 4 CH$_3$— | 6.2 | 74.7 | 100 |
| Prussic acid | 8.3 | | | | | | |

While the invention has been described in detail and with reference to specific examples thereof, it will be apparent to one skilled in the art that various changes and modifications can be made to these examples without departing from the spirit and scope of the invention.

What is claimed is:

1. A process for predominantly producing R(−)-mandelic acid or a derivative thereof represented by formula (I):

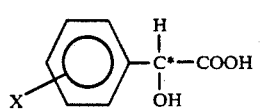

(I)

wherein X represents a hydrogen atom, a halogen atom, a hydroxyl group, an aliphatic saturated alkyl group having from 1 to 3 carbon atoms, an aliphatic saturated alkoxy group having from 1 to 3 carbon atoms, a thioalkyl group, an amino group, a nitro group, a phenyl group, or a phenoxy group, which is bonded to the o-, m-, or p-position; which comprises subjecting the following compound (i) or (ii)

(i) R,S-mandelonitrile or a derivative thereof represented by formula (II):

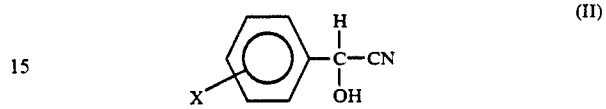

(II)

wherein X is as defined above, or (ii) a mixture of prussic acid and benzaldehyde or a derivative of benzaldehyde represented by formula (III):

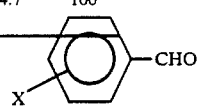

(III)

wherein X is as defined above; to the action of a microorganism selected from the group consisting of the genus Aureobacterium, Pseudomonas, Caseobacter, Alcaligenes, Acinetobacter, Brevibacterium, Nocardia, and Bacillus, which said microorganism is capable of stereospecifically hydrolyzing a nitrile group of said R,S-mandelonitrile or a derivative thereof represented by formula (II); in a neutral or basic aqueous reaction system to produce said R(−)-mandelic acid.

2. A process as claimed in claim 1, wherein said microorganism is *Aureobacterium testaceum* (IAM 1561), Pseudomonas sp. BC13-2 (FERM BP-3319), Pseudomonas sp. BC15-2 (FERM BP-3320), Caseobacter sp. BC4 (FERM BP-3316), Caseobacter sp. BC23 (FERM P-11261), Alcaligenes sp. BC12-2 (FERM P-11263), Alcaligenes sp. BC20 (FERM P-11264), Alcaligenes sp. BC35-2 (FERM BP-3318), Alcaligenes sp. BC24 (FERM P-12063), Acinetobacter sp. BC9-2 (FERM BP-3317), *Brevibacterium acetylicum* (IAM 1790), *Nocardia asteroides* (IFO 3384), or *Bacillus subtilis* (ATCC 21697).

3. A process as claimed in claim 1, wherein said aqueous reaction system has a pH of from 4 to 11.

4. A process as claimed in claim 1, wherein said aqueous reaction system has a pH of 6 to 10.

5. A process as claimed in claim 1, wherein said aqueous reaction system contains (i) 0.1 to 10% by weight of said R,S-mandelonitrile or a derivative thereof represented by formula (II); or (ii) 0.1 to 10% by weight of benzaldehyde or a derivative of benzaldehyde represented by formula (III) and 0.1 to 1.0% by weight of prussic acid.

6. A process as claimed in claim 1, wherein said aqueous reaction system contains (i) 0.2 to 5.0% by weight of said R,S-mandelonitrile or a derivative thereof represented by formula (II); or (ii) 0.2 to 5.0% by weight of benzaldehyde or a derivative of benzaldehyde represented by formula (III) and 0.1 to 0.5% by weight of prussic acid.

7. A process as claimed in claim 1, wherein said aqueous reaction system contains 0.01 to 5.0% by dry weight of said microorganism based on the weight of (i) said R,S-mandelonitrile or a derivative thereof represented by formula (II), or (ii) said prussic acid and benzaldehyde or a derivative of benzaldehyde represented by formula (III).

8. A process as claimed in claim 1, wherein said reaction is conducted at a temperature of 0° C. to 50° C. for 0.1 to 100 hours.

9. A process as claimed in claim 1, wherein said reaction is conducted at a temperature of 10° to 30° C. for 0.1 to 100 hours.

10. A process for predominantly producing R(−)-mandelic acid or a derivative thereof represented by formula (I):

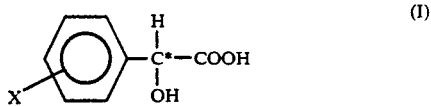

wherein X is a hydrogen atom, which comprises subjecting R,S-mandelonitrile or a derivative thereof represented by formula (II):

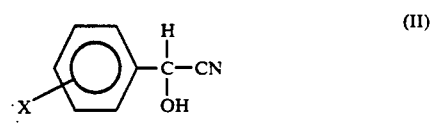

wherein X is a hydrogen atom, to the action of a microorganism of the genus Aureobacterium, which said microorganism is capable of stereospecifically hydrolyzing a nitrile group or said R,S-mandelonitrile or a derivative thereof represented by formula (II); in a neutral or basic aqueous reaction system to produce said R(−)-mandelic acid.

* * * * *